United States Patent

Eymin Petot Tourtollet et al.

Patent Number: 6,010,593
Date of Patent: Jan. 4, 2000

[54] PROCESS FOR REGULATING A PAPER PULP DEINKING LINE AND DEVICE FOR CONTINUOUSLY MEASURING THE QUANTITY OF PARTICLES CONTAINED IN A LIQUID

[75] Inventors: Guy Eymin Petot Tourtollet, Tencin; François Julien Saint Amand, Le Touvet; Bernard Perrin, Grenoble; Jacques Sabater, Gif Sur Yvette, all of France

[73] Assignee: Centre Technique de L'Industrie des Papiers, Cartons et Celluloses, France

[21] Appl. No.: 08/863,548

[22] Filed: May 27, 1997

[30] Foreign Application Priority Data

Jun. 10, 1996 [FR] France ..................... 96 07391

[51] Int. Cl.$^7$ ..................................................... D21B 1/08
[52] U.S. Cl. .............................. 162/4; 162/49; 162/263; 356/222; 356/335; 356/336; 377/10
[58] Field of Search ................................. 162/263, 49, 4, 162/198; 356/335, 336, 124, 36, 220, 222, 225; 209/17, 273; 377/10, 37, 53

[56] References Cited

U.S. PATENT DOCUMENTS

| | | | |
|---|---|---|---|
| 4,075,462 | 2/1978 | Rowe | 235/92 |
| 4,911,025 | 3/1990 | Soderling | 73/863 |
| 4,931,660 | 6/1990 | Mayer | 250/575 |
| 5,191,388 | 3/1993 | Kilham | 356/335 |

FOREIGN PATENT DOCUMENTS

| | | |
|---|---|---|
| 0539456 | of 0000 | European Pat. Off. . |
| 0059140 | 9/1982 | European Pat. Off. . |
| 0310740 | 4/1989 | European Pat. Off. . |
| 2297413 | 8/1976 | France . |
| 86/05525 | 9/1986 | WIPO . |
| 95/08019 | 3/1995 | WIPO . |

*Primary Examiner*—Dean T. Nguyen
*Attorney, Agent, or Firm*—Parkhurst & Wendel, L.L.P.

[57] ABSTRACT

A process and device for continuously measuring the quantity of particles suspended in a liquid, which exist in at least two different physical states, such as detached or attached within the paper pulp. A separation assembly separates the particles into divisions depending on their size, and the separation assembly is continuously fed with liquid via an input pipe. A measuring and processing assembly has two channels or ducts coming from the separation assembly and are provided with translucent windows. A measurement and capture unit illuminates the windows, and at least two cameras located opposite each of the respective windows are synchronized with the illumination unit to capture, at regular intervals, an image of the windows. A system for digitizing the captured images and processing them to determine the quantity of particles for each physical states is forwarded to an output unit in a digital or analog form.

15 Claims, 6 Drawing Sheets

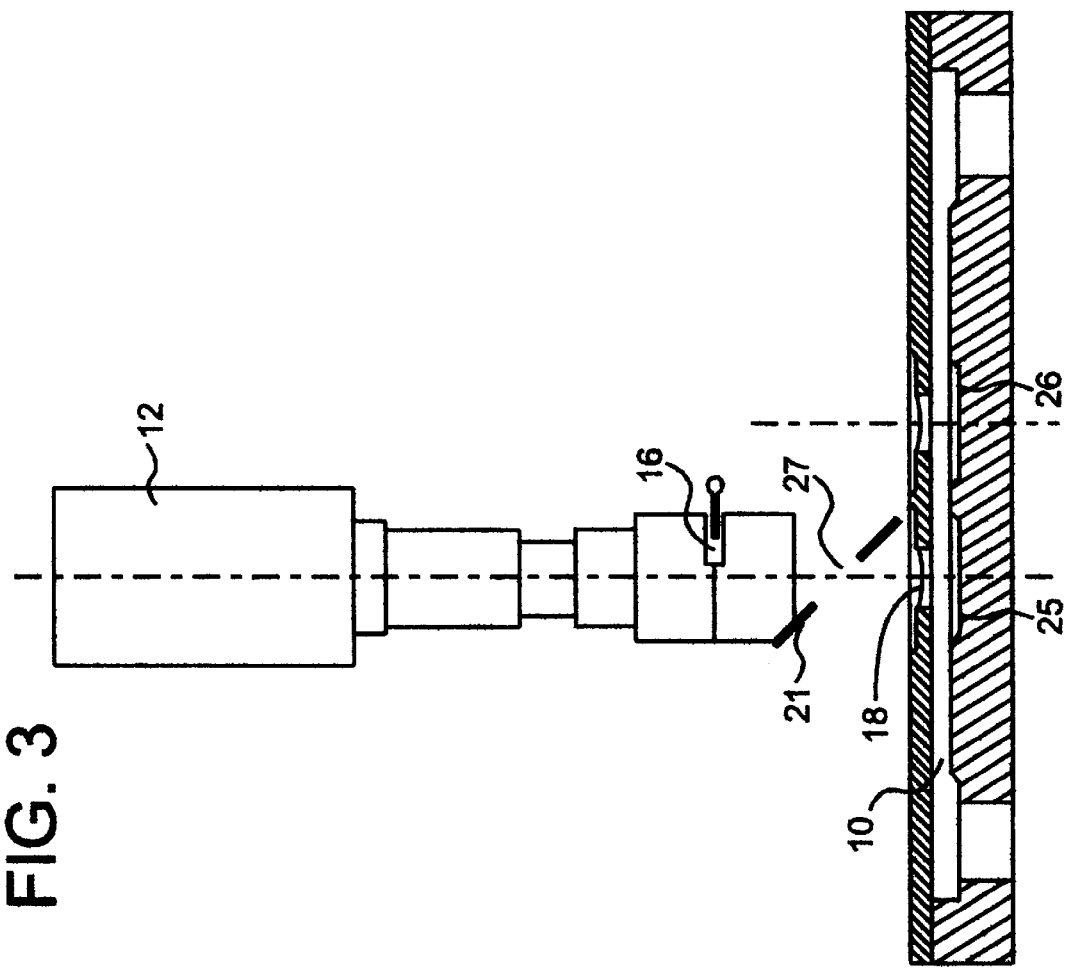
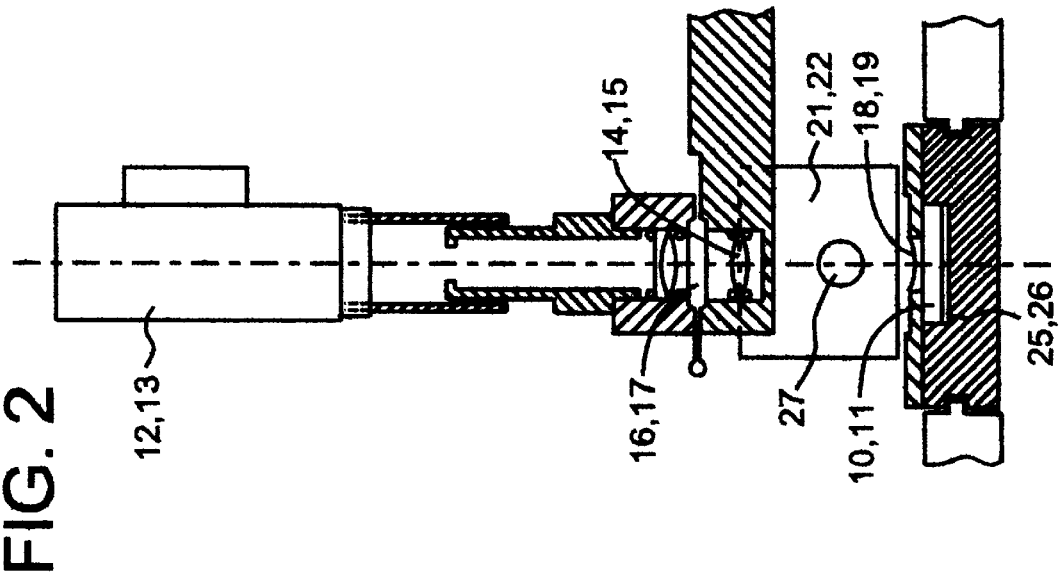

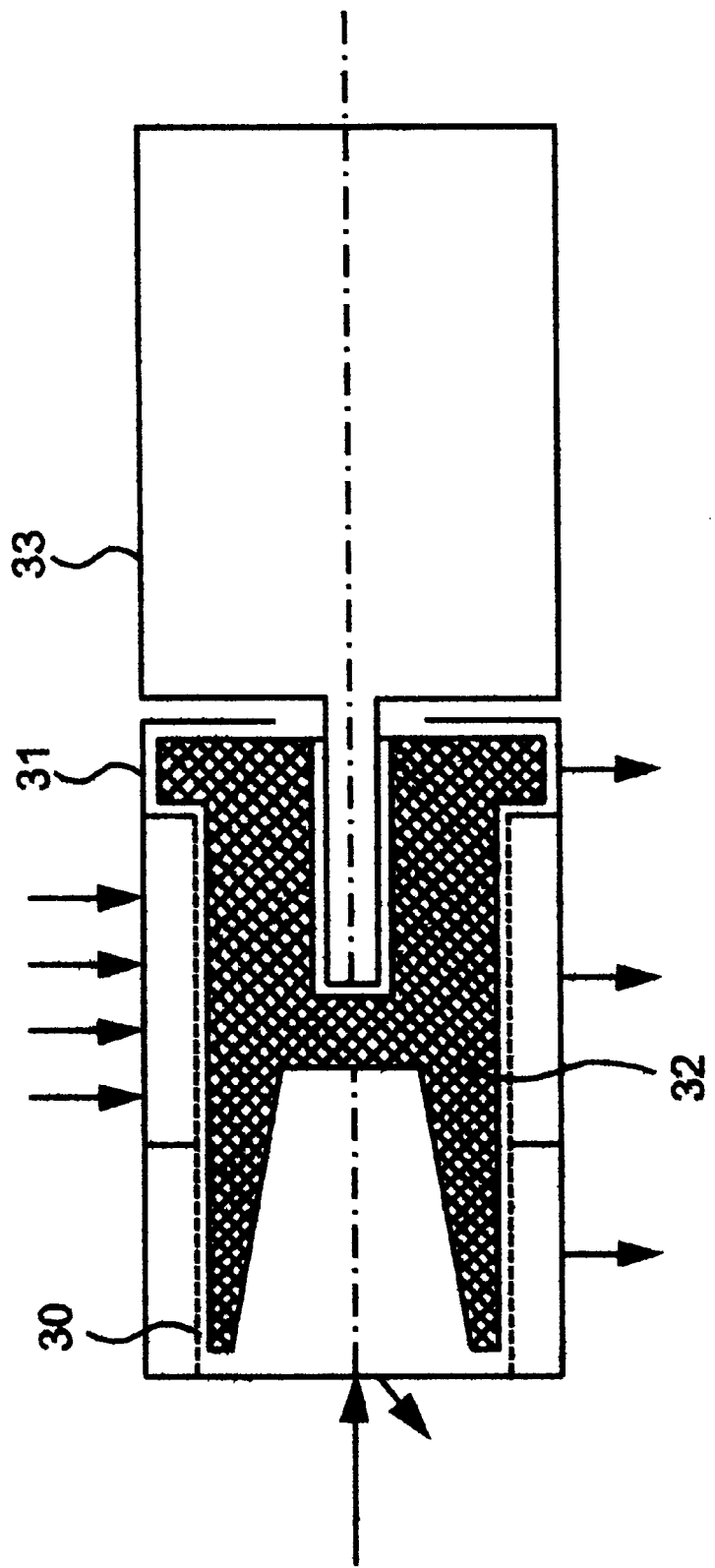

6,010,593

PROCESS FOR REGULATING A PAPER PULP DEINKING LINE AND DEVICE FOR CONTINUOUSLY MEASURING THE QUANTITY OF PARTICLES CONTAINED IN A LIQUID

BACKGROUND OF THE INVENTION

The invention relates to a process intended to allow regulation of a line for deinking a paper pulp obtained from recycled or reclaimed paper.

It also relates to the device capable of implementing this process and, more generally, to a device capable of continuously measuring the quantity of particles contained in a liquid, said particles being especially in two different physical states, in particular in the individualized state and in the state bonded to an entity of larger size, such as a fiber for example, these entities being in particular microscopic and being separated beforehand by mechanical means according to dimensional criteria.

The invention relates more particularly to the continuous separation, by screening and washing, of individualized microscopic particles in a suspension from microscopic particles bonded to other more voluminous entities in said suspension, separation being followed by a continuous measurement, by image analysis, on the separated suspension flows of the various fractions of particles.

As already mentioned, the invention is more particularly intended for the papermaking industry, especially for monitoring and regulating the operations of deinking paper pulps coming from reclaimed paper, by providing means for separately measuring the fractions of ink particles "attached to" and "detached from" the papermaking fibers, especially cellulose fibers, this being carried out directly and continuously in the pulp at various points in the deinking process.

Of course, although in the rest of the description the invention is more particularly described with regard to its application to the papermaking industry, it should not be understood to be limited to this single application, and it may also be employed in other fields requiring continuous and separate monitoring of microscopic particles in suspension, according to their nature, associated with dimensional criteria, especially in the field of water treatment and in that of the chemical or agrifood industries.

The recycling of reclaimed paper requires, in particular in the case of printed wastepaper which has to be recycled in the manufacture of white paper, especially of the graphics-paper type, the implementation of various deinking operations aimed at removing the printing inks associated with these materials. Removal of these ink particles necessitates first of all that they be individualized, that is to say correctly separated from the paper printing medium, and in particular that they be detached from the fibers so as to be able to be selectively extracted from the suspension of recycled fibers.

The separate and continuous control of the attached and detached ink particles proves to be very advantageous whenever the ink-detaching operations, especially pulping and hot slushing, and the ink-removal operations, especially washing and flotation, make use of different technologies and different chemical auxiliaries.

Conventionally, the deinking processes include most of the following steps :

making a pulp from wastepaper by pulping, that is to say by mechanical action in the presence of chemicals which promote defibering of the paper and detachment of the ink from the fibers ;

precleaning, by screening on a screen having holes and slits and by cycloning, intended to remove the voluminous and heavy impurities ;

deinking by flotation and/or washing, aimed at removing the ink particles provided that they have been separated from the fibers during pulping ;

fine cleaning by slit screening and cycloning in order to remove small impurities, both heavy and light;

hot treatment aimed, on the one hand, at detaching the ink particles remaining fixed to the fibers and, on the other hand, at dispersing or fragmenting the residual impurities to below the visibility threshold (printing fragments and various impurities, especially those which are heat-fusible); and bleaching of the pulp, possibly combined with hot dispersion when the bleaching products are introduced upstream of the hot treatment.

Other steps may be added to these operations, in particular when the quality requirements of the deinked pulp are very high in terms of whiteness and cleanness. These steps essentially consist of:

postdeinking by flotation and/or washing, intended to remove inks which have been detached during hot dispersion;

postcleaning by screening through fine slits and/or cycloning, for finishing off the cleaning, especially because of the shape modifications undergone by impurities of the type generally referred to by the term "stickies" (glues and adhesives) during the hot treatment;

final hot treatment for dispersing the residual impurities and inks to below the visibility threshold;

complementary bleaching of the type which is in principle different, that is to say reducing when the first bleaching is oxidizing, and vice versa.

The size of the ink particles in recycled pulps is typically of the order of a few micrometers. The size distribution of these particles can vary considerably depending on the nature of the inks, that is to say can include sizes below one micrometer, in the case of certain inks of the water-soluble type (flexographic printing, etc.), or in the visible range even up to several hundreds of micrometers, in the case of certain inks of the heat-fusible type (laser inks, etc.).

DISCUSSION OF THE PRIOR ART

At the present time, various possible ways exist for the continuous monitoring, directly in the pulp, of contrasted particles. However, the techniques currently proposed are limited to the measurement of particles having sizes greater than the visibility threshold. A monitoring device for particles of this type is described, for example, in document EP-B-0,539,456.

Such a monitoring device basically comprises a branch pipe provided with a transparent window opposite which is placed a pulsed light source, intended to illuminate said window, and a camera intended to detect the contrasting impurities by backscattering and to measure them, in such a way as to extract from the signals thus captured the apparent surface area of each of said impurities and the quantity of impurities. This device also includes digitizing and processing means so as to reproduce from this data a visual and exploitable shape.

These in-line techniques for measuring black spots constitute effective monitoring means for certain aspects of the deinking but do not make it possible, however, to monitor the aspects relating to the essential criterion of the whiteness of the pulp, namely the removal of microscopic inks and their prior detachment.

The in-line means for monitoring these essential aspects of the deinking are currently limited to measuring the whiteness of the pulp in liquid medium using backscattered-light analysis techniques.

These whiteness measurements provide information about the variations in quality of the raw material and/or in effectiveness of the deinking operations, but they do not allow evaluation either of the effectiveness of the ink removal or, a fortiori, the effectiveness of the detaching operation insofar as the whiteness of pulps is greatly affected by their composition in terms of mineral fillers and fibers of various origins.

Thus, insufficient whiteness at the end of the deinking line may be due to very different causes, such as for example limited flotation effectiveness, the presence of ink which is difficult to detach, or poor bleaching conditions which may not be detected by the in-line whiteness measurements.

Laboratory techniques are also used for evaluating the deinking, but they do not allow in-line monitoring and require sample removal and preparation procedures as well as the execution of relatively lengthy and tedious measurements. Among these, mention may be made of the overall measurement of the ink content obtained by analyzing the reflectance in visible light and in the near infrared, this measurement being performed on samples of pulp which has been washed or thickened on a filter after adding flocculents, but also the direct measurement of the ink particles obtained by microscope image analysis, this being carried out on various preparations of samples of pulp, of washed fibers or of filtrates deposited on microfilters.

GENERAL DISCUSSION OF THE INVENTION

The object of the invention is to remedy these drawbacks and to overcome the limitations of the current in-line means for monitoring the deinking.

It relates in particular to means for continuously separating, by screening and washing, the attached ink particles from the detached ink particles, in suspension in paper pulps coming from reclaimed paper, these means being combined with means for continuously measuring the quantities and sizes of these two ink particle fractions by image analysis on the flows of the separated suspensions.

More generally, it relates to a device for continuously measuring the quantity of particles which exist in different physical states, in suspension in a liquid. This device comprises:

a unit for separating the particles into fractions having different sizes and concentrations in said liquid, said unit being fed with liquid via a suitable pipe;

two channels or ducts coming from said separating unit and conveying said fractions to a measurement zone, each channel or duct having a transparent window in this zone;

a measurement and capture assembly comprising:

a unit for illuminating said windows;

two cameras located opposite each of said windows, synchronized with said illumination unit and intended to capture, at regular intervals, an image of the windows;

means for digitizing the images thus captured and for processing them, these means being intended to determine the size and quantity of said particles;

a unit for outputting the data determined in this way, especially to a sensory reproduction unit, or in the form of analog or digital signals intended to actuate one or more defined units.

According to one characteristic of the invention, the separating unit also provides a function of washing the suspension thus subjected to analysis.

This separating and washing unit comprises a cylindrical microperforated screen within which continuously rotates a declogging and screening rotor, the axis of rotation of which is collinear with the axis of the screen, said rotor creating pressure pulses and forcing the liquid to the internal surface of the screen.

The subject of the invention is also a process for regulating a line for deinking a paper pulp coming from recycled paper, which consists in continuously measuring the quantity of ink particles in suspension in two different physical states, respectively particles that are individualized within the pulp and particles that are bonded to other more voluminous particles, and especially to the papermaking fibers, and then, depending on the measurements thus made, in acting on the various operating parameters of the deinking line, especially during the pulping and hot slushing steps, and during the washing and flotation steps.

The manner in which the invention may be realized and the advantages which stem therefrom, as well as its applications, will become clearer from the embodiments which follow, given by way of nonlimiting indication and supported by the appended figures.

DISCUSSION OF THE DRAWINGS

FIG. 2 is a diagrammatic cross-sectional representation of a detail of FIG. 1.

FIG. 3 is a longitudinal sectional representation thereof.

FIG. 4 is a diagrammatic representation of the device for separating and washing a paper pulp in accordance with the invention.

The description which follows relates to a setup intended to be mounted in a paper pulp deinking line. As already mentioned, it is obvious that the invention should not be understood to be limited to this single application.

DETAILED DESCRIPTION OF THE INVENTION

Figure 1:
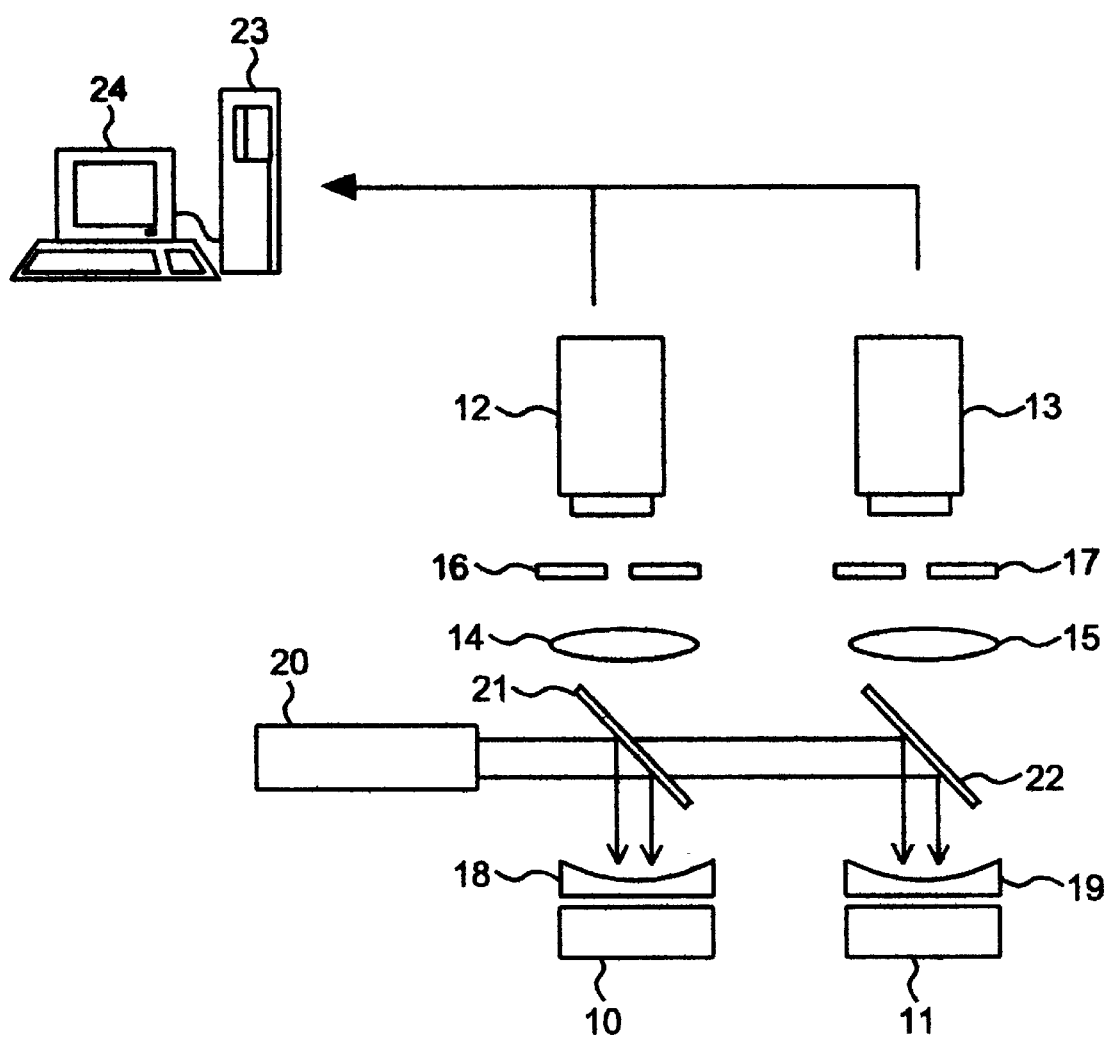
FIG. 1 is a diagrammatic representation of the setup in accordance with the invention.

FIG. 1 shows very diagrammatically part of the setup forming the subject of the invention. In fact, FIG. 1 shows the analysis and treatment part, this therefore lying downstream of the mechanical separating and washing part described below in more detail.

Basically, this analysis part includes two channels of the duct type (10) and (11), fed respectively with concentrated filtrate, also called liquor, and with washed pulp, essentially consisting of fibers leaving the mechanical part described below.

The liquor and fibers therefore flow continuously through these channels (10) and (11). These channels are each provided with a transparent window above each of which is oriented, normal to the windows, a camera of the CCD type, respectively (12) and (13), optionally preceded by suitable optical components, such as lenses (14) and (15) and apertures (16) and (17), said apertures being adjustable, of course.

Moreover, in order to optimize the surface analyzed, plano-concave lenses (18, 19) are placed above said windows.

These windows are illuminated by means of a pulsed light source (20), typically a stroboscope, advantageously a single one for both ducts, the setup being provided for this purpose with a first splitter plate (21) and with a semi-transparent mirror (22). The plate (21) and the mirror (22) are furthermore drilled with a central hole (27) intended to allow capture by the cameras (12, 13) of the data from the windows of the ducts (10, 11). The operation of the cameras (12) and (13) and of the stroboscope (20) is managed by an electronic assembly which synchronizes the flash of the stroboscope with the operation of the cameras, and especially with their frame scanning.

Of course, this stroboscope may be replaced by any pulsing system, or even by a ring of LEDs (light-emitting diodes) which are sufficiently powerful to provide a lighting level compatible with very short illumination times. This is because, given the size of the particles to be detected, it is desirable to achieve a resolution of at least three microns, with a pulp flow rate in the ducts (10) and (11) of the order of 1 m/s, so that the illumination time is of the order of one microsecond.

As shown in FIG. 1, the two cameras (12) and (13) are linked to a processing unit (23), typically a microcomputer, within which are stored, in a suitable memory, the digitized images captured by said cameras. Each of the images thus digitized is processed by the unit (23) so as to detect the presence of the desired particles as well as their size. These particles are in fact detected by backscattering.

This processing is managed by software, of a type known per se for this application. In this specific case, this processing assembly (23) has two video inputs which are analyzed in quasi-real time by said software. This results in a number of particles per unit volume as well as the surface area of these particles. This information may be reproduced on the screen (24), for example in the form of histograms. Moreover, this information may be printed by means of a conventional printer, or even sent via an output of the processing unit (23) in the form of analog or digital signals to be used by any processing system, as will be described later.

The cameras/flash assembly is mounted so as to be free running with respect to the unit (23) at a rate of 25 images per second, i.e. 50 frames per second.

As already explained, the cameras and the stroboscope or equivalent system are synchronized with respect to each other. Thus, when the processing of one image has been completed, said unit (23) commands the cameras/stroboscope assembly to restore a new digitized image of the ducts (10) and (11)to it. In this way, the time intervals separating two successive analyses are short for the purpose of optimizing the accuracy of the setup by reducing the statistical error, given the increase in the number of measurements made.

Furthermore, and in order to optimize detection by the cameras, that face of the ducts (10, 11) which is opposite the windows is advantageously provided with an appropriate background (25, 26), of a particular color, and chosen depending on the opacity of the pulp and on the depth of field of the cameras.

FIGS. 2 and 3 show a more detailed representation, respectively in cross section and in longitudinal section, of the cameras and the ducts.

A more detailed description will now be given of the mechanical part for separating and washing the pulp, which part is therefore located upstream with respect to the processing part described previously. This mechanical part (see FIG. 4) basically comprises a cylindrical microperforated screen (30) mounted in a casing (31) which is also of cylindrical shape. This microperforated screen is intended to separate the fibers from the fine elements contained in the recycled pulp. Typically, it consists of a sheet made of stainless steel 1 or 2 millimeters in thickness, through which pass holes which have a diameter of between 0.1 and 0.3 millimeters and are separated by between 1 and 3 millimeters. In one embodiment of the invention, the internal diameter of the cylindrical screen is 120 millimeters for a length of 200 millimeters.

A declogging rotor (32) is made to rotate inside the screen (30) by means of a motor (33) outside the casing (31). As may be more clearly seen in FIG. 5, this rotor is composed of three parts, a central first part (34) mounted on the output axis of the motor (33), an axisymmetric second part (35) and, at the end of the part (34), a likewise axisymmetric third part (36) located substantially in the extension of the part (35), said second and third parts being fastened to said first part.

Furthermore, the part (35) is provided with parallel radial separating disks (37) intended to delimit successive washing, diluting and thickening zones. In fact, the device described includes dilution-water inlets (38) by means of tubes fixed to the casing (31), these tubes being provided on the periphery of the casing. Each of these inlets (38) in fact includes a nozzle for injecting dilution water through the screen (30). The separating disks (37) each have skew-cut notches, provided on the periphery of the disks (37) and inclined with respect to the direction of rotation, in such a way as to encourage the transfer of thickened pulp from one washing zone to the next. The diluted filtrates extracted from the washing zones are recycled in the deinking process, as well as the fractions after analysis. In fact, these diluted filtrates are collected in a channel (39), for the purpose of this subsequent recycling.

Figure 5:
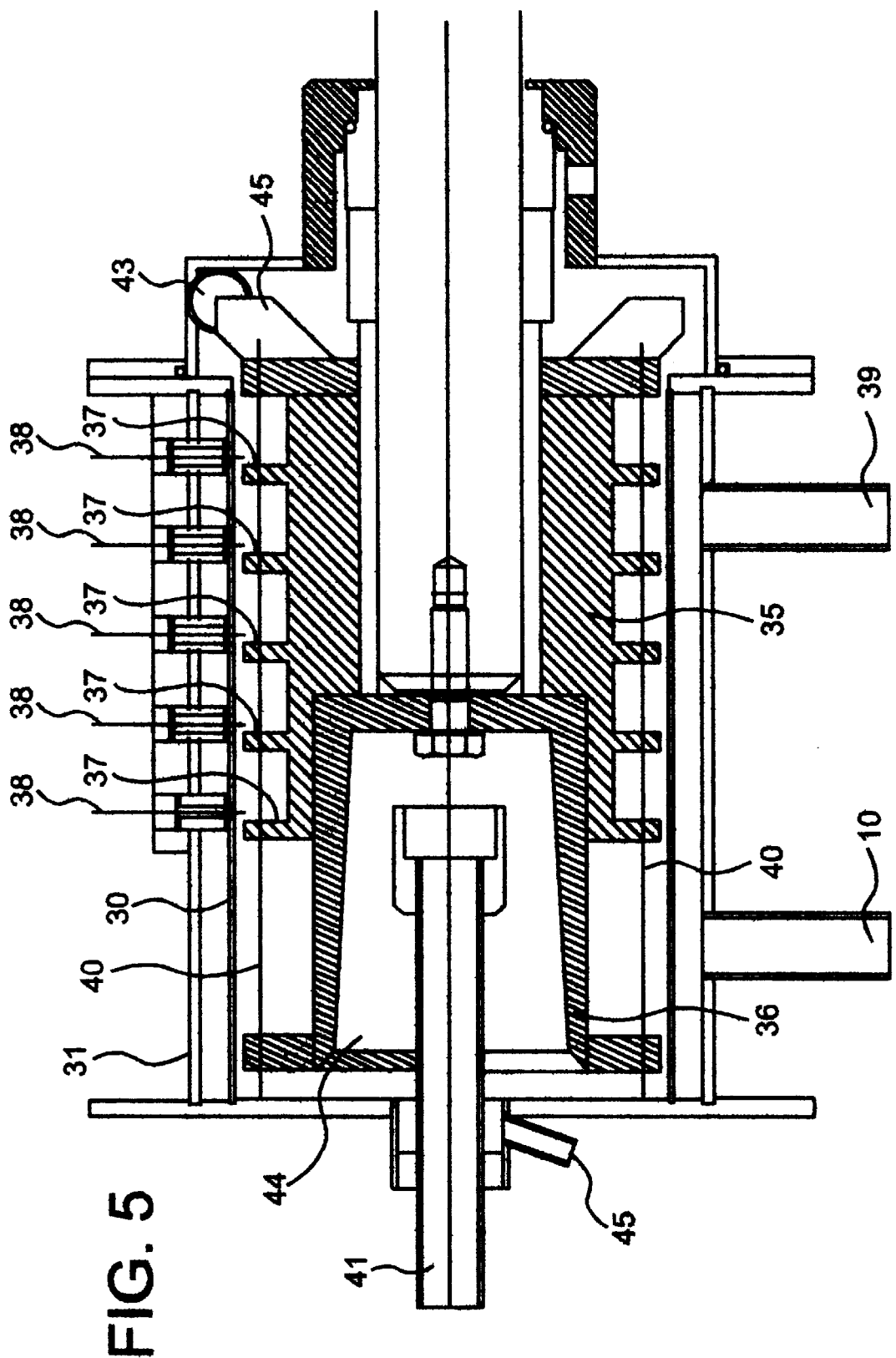
FIG. 5 is a more detailed sectional view of FIG. 4.

The rotor (32) is composed of two diametrically opposite declogging cylinders (40) which pass through the separating disks (37) and are shown, in FIG. 5, by their spindle (40).

The part (36) of the rotor (32) defines a deaeration chamber (44) in which a pipe (41) for supplying the paper pulp to be analyzed terminates. In fact, the pipe (41) is fed directly with paper pulp during the deinking step. This sampled pulp has a concentration of approximately 1% and is diluted upstream of the device, if necessary.

In fact, on account of the position of the pipe (41), which lies along the axis of rotation of the rotor (32), and also on account of the rotation of the rotor and of the volume of the deaeration chamber, dimensioned so as to have a sufficient residence time, a pulp-pumping and -deaerating effect is produced. The air is expelled via the outlet pipe (45) provided near the region where the pipe (41) enters the casing (31).

Next, the pulp is thickened up to a concentration of approximately 3% in a first screening zone (42), for screening through the screen (30), because of retention of the fibers. The fine elements, containing fibers, fillers and detached ink particles, pass through the screen and feed one (10) of the two measurement ducts mentioned when describing the processing part of the setup. In the absence of dilution, the filtrate coming from this zone remains relatively concentrated, which avoids having to reduce the number of ink particles subjected to measurement.

The rotor (32) has fins (45) for pressurizing the pulp coming from the washing zones. Provided opposite the deaeration chamber (44) is a tangential outlet (43) through which the fraction of washed fibers passes. This tangential outlet (43) feeds the second duct (11) for measurement of the ink particles attached to the fibers. This pulp fraction also contains ink particles which are not bonded to the fibers but are retained by the screen, because of their size. This fraction therefore contains "black spots", which may or may not be bonded to fibers, and in a quantity generally much less than the quantities of ink particles attached to the fibers (ink covering the surface of the fibers or particles of various sizes which are fixed to fibers, depending on the type of ink).

As already stated, the declogging elements (40) of the rotor consist of portions of a cylinder whose spindle (40), parallel to the screen (30), passes through the various separating disks (37) of the washing sections. The choice of declogging cylinders, instead of foils, that is to say of conventional declogging elements having a cross-section in the form of aircraft wings, means that construction and adjustment are made easier.

Typically, the diameter of the declogging cylinders is between 6 and 12 mm and the actual gap between the cylinders and the screen is between 1 and 3 mm.

The diameter of the screen is preferably between 100 and 150 millimeters for a length of between 150 and 300 millimeters. These dimensions ensure that the pumping and deaeration effects are produced in the pulp for flow rates of the order of 0.1 m$^3$/h at each of the outlets (10, 39 and 43) and for rotation speeds of from 1000 to 2000 revolutions per minute, depending on the diameter of the rotor, and preferably from 1500 to 1800 revolutions per minute for a diameter of 120 millimeters.

Under these conditions, the declogging pressure-pulsing and pumping pressures vary from 0.1 to 1 bar ($10^4$ to $10^5$ pascals), preferably from 0.2 to 0.7 bar ($2\times10^4$ to $7\times10^4$ pascals). The residence time of the pulp in the deaeration chamber (44) is of the order of 10 seconds and the centripetal accelerations are a few hundred m/s$^2$, thereby ensuring the separation of air bubbles up to approximately 30 μm in diameter, that is to say the removal of most of the air bubbles remaining in the pulp, especially after flotation, said bubbles being discharged via the outlet (45).

On account of the size of the perforations in the screen (30), this allows only the fine elements (fines, fillers and inks) to pass through and retains the fibers, contrary to the conventional screening devices which are intended to let the fibers through and to retain the contaminants.

In another embodiment of the invention, the separating disks (37) of the successive washing zones are replaced by a screw, the pitch and radial extension of which correspond to those of the disks, thereby leading to continuous washing by dilution and successive thickening along the helicoidal channel thus formed.

The direction of inclination of the screw is defined by the direction of rotation of the rotor so as to ensure that the pulp is removed to the washed-fiber outlet (43) due to the effect of rubbing of the suspension on the surface of the screen.

In order to reduce the consumption of washing water, the external annular chamber at the screen (30) advantageously includes a spiraled partition defining a helicoidal channel which is of the type similar to that of the rotor (32) but which is stationary and lying downstream of the screen (30). The outlet for the diluted filtrates is omitted and the water feeds (38) are replaced by a single washing-water feed at the end of the stationary spiraled channel lying on the side facing the washed-fiber outlet (43).

Under these conditions, the filtrates passing through the screen in the overpressure phase are pumped back through the screen in the underpressure phase created by the declogging cylinders (40) of the rotor, leading to countercurrent washing of the fibers upstream of the screen (30) by the dilution water, and then the decreasingly diluted filtrates flowing through the stationary spiraled channel to the outlet (10) for the concentrated filtrates. Advantageously, the rotor is equipped with a larger number of declogging cylinders (40) so as to increase the duration of the underpressure phases.

Figure 6:
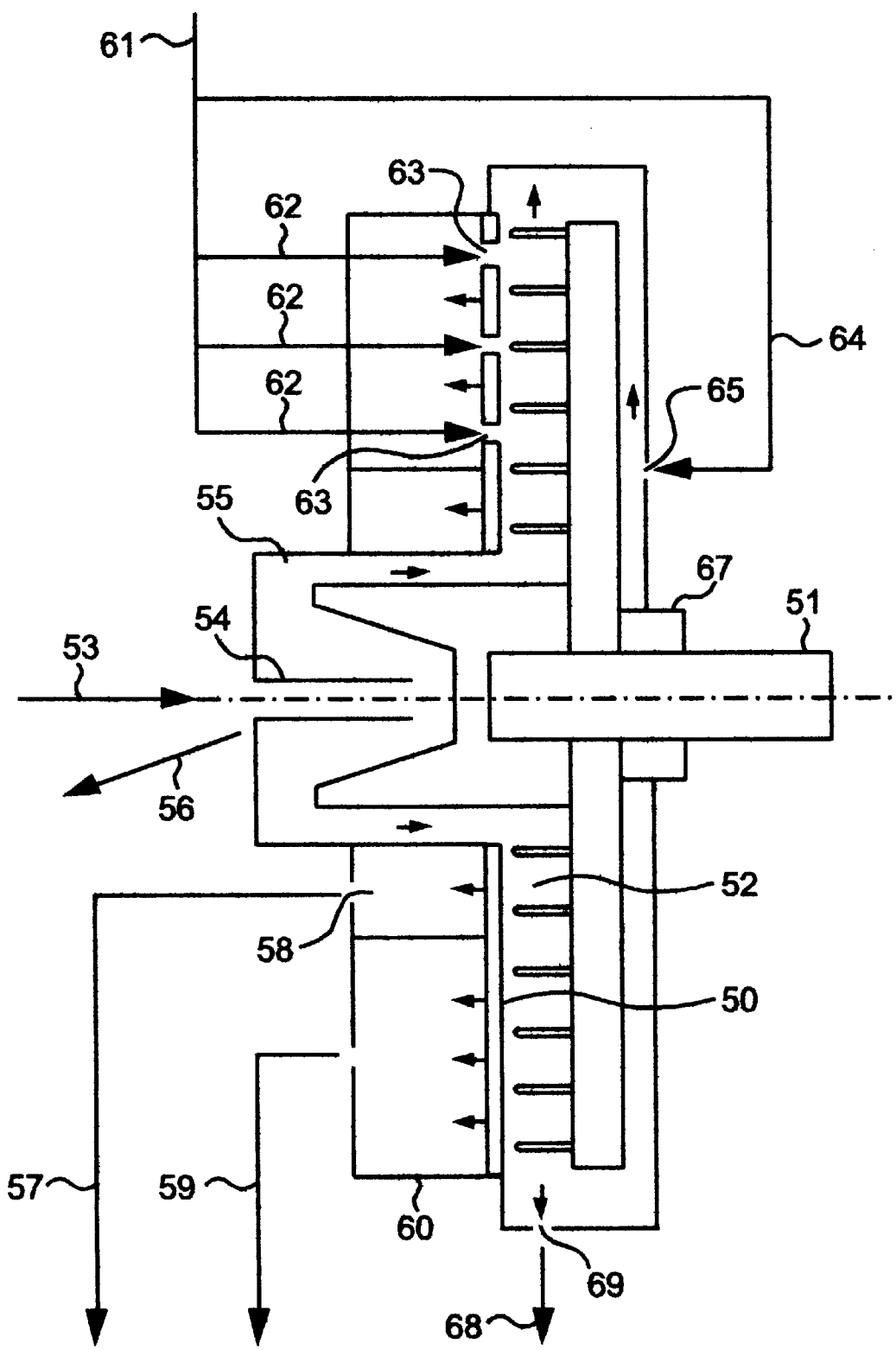
FIG. 6 shows another embodiment of the device of FIGS. 4 and 5.
Figure 7:
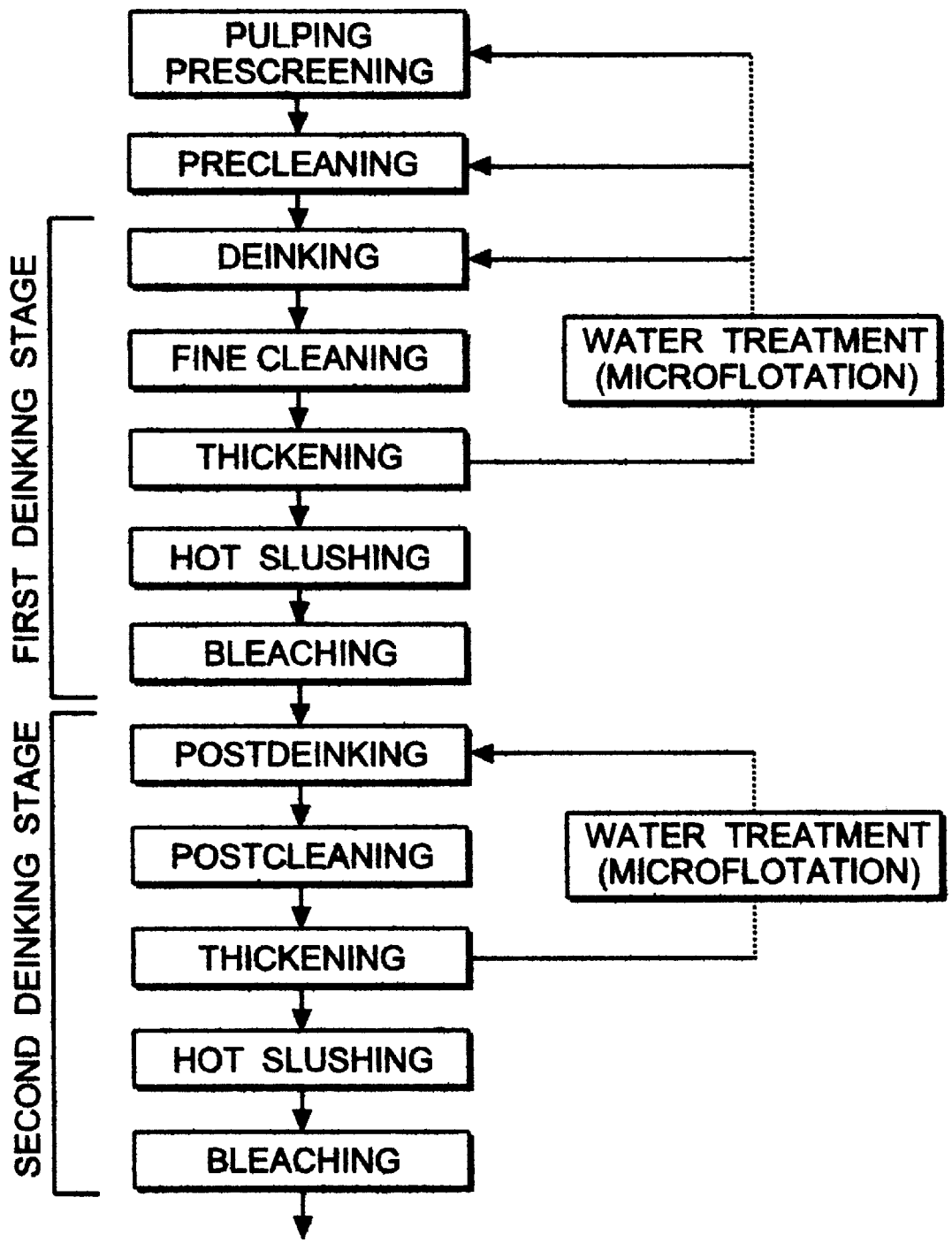
FIG. 7 is a simplified form of a diagram representing the various treatment steps in a deinking line.

According to another embodiment of the invention, shown in FIG. 6, the separating screen may be flat and in the form of a microperforated flat disk (50). The rotor (51) may also be flat and have a spiraled channel (52) providing the centrifugal flow of the pulp and then of the washed fibers.

The device is fed (at 53) along the axis of the rotor (51) via a tube (54) emerging in a chamber (55) so as to allow removal of the air (at 56) under conditions similar to those described previously.

Next, the pulp is driven towards the spiraled channel (52) which also provides the pumping and declogging effect for the screen (50).

The concentrated filtrates are extracted (at 57) from the annular chamber (58) and the diluted filtrates are extracted (at 59) from the annular chamber (60).

The dilution water is introduced (at 61), on the one hand, at various points (62) by means of tubes (not shown) which pass through the chamber (60) and the screen (50) via holes (63) and, on the other hand (at 64), via a hole (65) made in the wall close to the sealing device (67) so as to avoid accumulation of pulp at the rear of the rotor and to dilute the washed fibers extracted (at 68) via a tangential outlet (69).

In order to reduce the consumption of washing water, the cylindrical partition separating the annular chambers (58) and (60) is advantageously replaced by a spiraled partition which is of the type similar to that defining the spiraled channel of the rotor (51) but which is stationary and located downstream of the screen (50). The outlet (59) for the diluted filtrates is omitted and the water feeds (62) are replaced by a single washing-water feed at the peripheral end of the stationary spiraled channel downstream of the screen (50).

Under these conditions, the filtrates passing through the screen in the overpressure phase are pumped back through the screen in the underpressure phase created by the rotor, resulting in countercurrent washing of the fibers upstream of the screen (50) by the dilution water and then the decreasingly diluted filtrates flowing through the stationary spiraled channel to the outlet (57) for the concentrated filtrates.

Various applications of the invention are described below, especially within the framework of the regulation of a line for deinking pulp coming from recycled or reclaimed paper.

Many studies have been able to show that the parameters influencing detachment of the ink during pulping, that is to say in the pulper, and the hot treatment (hot slusher or disperser) essentially consist of the mode of action (type of equipment and concentration of the pulp), specific energy, temperature, chemical auxiliaries and, of course, the type of ink.

It has also been demonstrated that the parameters influencing the removal of ink by flotation or by washing essentially depend on the technology used, on the physico-chemistry of the medium and on the characteristics of the inks (surface properties and particle size distribution).

Given that these parameters are so manifold, many applications of the device according to the invention are conceivable. Indeed, the device for separating and continuously monitoring the ink fractions may advantageously be combined with a whiteness measurement (using known means) on each of the fractions.

Thus, the examples described below illustrate, for various arrangements of the device for continuously monitoring the attached and detached inks, a few possible ways of regulating some of the essential steps in the deinking process.

Example I: Arrangement of the monitoring device at the beginning of the deinking line The device may be arranged at the beginning of the line only after the wastepaper has been pulped and coarsely screened, that is to say at the precleaning stage after the draining tank of the pulper (after continuous or discontinuous prescreening through holes, depending on the type of pulper). An arrangement at the end of precleaning has the advantage of making it easier for continuous sampling of the pulp (lower concentration) and of avoiding the risks of a blockage of the device for separating the ink fractions due to coarse contaminants.

Under these arrangement conditions, acting upstream on the pulping conditions may be envisaged only after a delay time corresponding approximately to the pulping time. Despite this delay, the specific pulping power, especially the pulping time, and the auxiliaries may be regulated depending on the quantities of attached ink and on the fragmentation of the detached ink particles.

Thus, when a batch of wastepaper bales includes inks which are difficult to detach, the monitoring device according to the invention makes it possible to increase the specific pulping power and/or the alkalinity so as to improve detachment, in particular when the deinking setup does not include hot treatment.

In contrast, when a batch of wastepaper includes easily detachable and/or dispersible inks (inks of the water-soluble type coming especially from newspapers printed using flexography), detection of detached and/or strongly fragmented inks enables the opposite measures to be taken at the pulping stage.

Example II: Arrangement of the monitoring device at the first deinking stage

Analyzing the pulp after deinking by flotation or washing, that is to say at the fine cleaning stage, allows more precise monitoring of the ink fractions because of the fact that most of the ink, which is detached at pulping, has been removed at deinking.

At this stage, the residual presence of ink particles in the filtrates of the separating device, detected by the monitoring device according to the invention, means that the flotation or washing is insufficiently effective. The various possible ways of regulating the deinking depend on the technologies used and on the design of the equipment.

Regulating the flotation, as a result of monitoring the detached ink, may be based either on controlling the addition of deinking products or on controlling the essential flotation parameters, in particular the amount of air, the size of the bubbles, the concentration, the degree of recycling and the scrap rate. However, these parameters are not independent and may vary only within certain limits defined by the type and design of the equipment.

By way of example, the technological parameters regulated may be the amount of tailings (froth) and/or the degree of recirculation around the flotation cells, if the design of the plant suffices.

Increasing the feed rate, and therefore the degree of recirculation for a constant concentration and constant production rate, leads, in the most common case of injector-type cells, to an increase in the feed pressure and in the airflow, thereby improving the effectiveness of the deinking to the detriment of the material yield and the energy consumption.

Increasing the volume fraction of tailings leads to a complementary improvement in the effectiveness of deinking. It should be noted that this increase in the amount of tailings from the primary cells, installed in line, means that the capacity of the secondary cells treating the tailings from the primary cells must be large enough and/or that the fraction of untreated primary tailings must be increased, that is to say the froth from the first primary cells which is generally rejected since it is highly charged with ink. These conditions reduce the yield significantly.

Regulating the flotation concentration constitutes another useful way of improving the effectiveness of deinking insofar as a reduction in the concentration reduces the losses, thereby making it possible, if necessary, to increase the flow rates and degree of recirculation without affecting the yield.

However, this way of regulating requires equipment of large enough capacity, especially at the thickening stage which often limits the production rate. In other words, it will then be a question of reducing the production rate in order to improve the quality.

Advantageously, for some pulp-thickening equipment, it is possible to reduce the retention of fine elements and of small detached ink particles which are thus recycled upstream of the flotation cells, thereby improving the effectiveness of deinking to the detriment of the yield. In other words, this way of regulating the operation of the thickening equipment amounts to supplementing the flotation with partial washing of the pulp.

Regulating the washing, on the basis of monitoring the detached ink, may be based either on controlling the parameters which vary the selectivity of the washing (retention of the fine elements and of the ink particles, this retention being determined by the physico-chemical and hydrodynamic conditions upstream of the screen or of the wire) or on controlling the degree of washing, that is to say the pulp-thickening factor. There are thus many possible ways of regulating the washing, these being peculiar to each of the various washing technologies currently used.

By way of example, the washing on selective thickening equipment, on wires derived from papermaking machines, may be regulated by controlling the speed of movement of the wires, thereby leading, for a constant washed-pulp production rate, to variations in the grammage of fibers deposited on the wire and therefore to variations in the retention of the ink particles and fine elements. In this case, and in general, the improvement in the deinking will be to the detriment of the yield.

The possible ways of regulating the deinking, on the basis of monitoring the ink particles in the fraction of washed fibers from the separating device relate more particularly to other steps in the process. The ink particles measured in this fraction mostly correspond to ink particles attached to fibers, as well as to the black spots (ink particles of "visible" size) which may or may not be bonded to fibers.

The monitoring of the black spots may be used in regulating the deinking steps which enable them to be removed, namely, in the main, the flotation step, the cycloning step and the hot treatments in the disperser or slusher.

With regard to flotation and cycloning, regulation based on controlling the concentration is particularly effective insofar as dilution at flotation and at cycloning, together with increasing the head losses which result therefrom, especially at cycloning, are the main operating parameters enabling the effectiveness of black-spot removal to be improved.

With regard to the hot treatment, the technological parameters enabling the dispersion of black spots to be improved are essentially the same as those enabling the detachment of ink particles to be improved.

Regulating the dispersion or hot slushing on the basis of monitoring the attached ink particles may advantageously be based on controlling the specific power, insofar as the energy consumption of the treatment is high, i.e. from 30 to 100 kWh/t for the disperser or slusher, outside the specific energy necessary for heating and for thickening the pulp.

The energy saving obtained by regulating a hot treatment depends on the variations in the compositions of the raw materials. The saving may be up to 20 to 50 kWh/t when the batches of wastepaper treated only periodically contain inks difficult to detach, which makes it possible to work most of the time at low specific power at the stage of a hot treatment regulated depending on the ink quantities measured in the washed-fiber fraction of the separating device. Under these conditions, regulating the hot treatment also makes it possible to avoid, most of the time, certain types of damage to the fibers which are observed at the high specific powers necessary for detaching the most difficult inks.

Regulating the temperature of the hot treatment, depending on the quantities of attached ink, also offers possibilities of energy saving, but it is more difficult to optimize this parameter in that, whereas detachment of inks of the heat-fusible type is often improved at high temperature, they are generally not fragmented so much.

Regulating the quantity of chemical auxiliaries introduced into the hot treatment in principle concerns only setups which include a bleaching stage downstream of the slusher or disperser, which therefore acts as a mixer and partially as a reactor for the bleaching products. This way of regulating the hot treatment in combination with the bleaching step may be carried out on the basis of the monitoring of attached ink, either upstream of the hot treatment at the first deinking stage or downstream of this treatment, in particular at a second deinking stage.

Advantageously, the combined regulation, of the heat treatment and the bleaching, may be based on monitoring, on the one hand, the attached ink and, on the other hand, the whiteness and, if necessary, the color, these being measured on the washed-fiber fraction of the separating device.

Measuring the components of the color (the Lab coordinates: a representation of the colors, calculated from the reflectance spectrum obtained with a resolution of from 10 to 20 nm) also makes it possible to match the type of subsequent bleaching to the coloring of the pulp. Thus, insufficient whiteness of the fibers may be corrected either by increasing the dose of bleaching agents or by carrying out another type of bleaching (especially hydrosulfite or FSA (formamidinesulfinic acid) bleaching) matched to the decoloring of the pulp, when the ink is detached from the fibers (which also promotes detachment in cases of bleaching in alkaline medium, especially hydrogen peroxide) or by increasing the specific power of the hot treatment, when the inks are insufficiently detached from the fibers and if the improvement in detachment of the ink is followed by its removal at a second deinking stage.

Example III: Arrangement of the monitoring device at the second deinking stage

Analyzing the pulp after a first deinking stage, that is to say after removing most of the ink by flotation and/or washing and detachment of the ink by hot treatment, followed in general by a first bleaching stage, makes it possible to monitor more particularly the residual ink particles which are difficult to detach and/or have not been removed sufficiently.

Advantageously, the device for continuously monitoring the attached and detached ink particles may be arranged at the postdeinking stage, that is to say after dilution downstream of bleaching, so as to improve the conditions for sampling the pulp and to benefit from the possibilities of combined monitoring of the bleaching and hot-treatment.

At this stage, the possibilities of regulating the postdeinking on the basis of monitoring the attached and detached ink particles are similar to those described previously, with additional possibilities of regulating upstream and downstream of the measurement in the case of sophisticated deinking setups which include two bleaching and hot-treatment stages.

For all these possibilities of regulating the various deinking steps, based on monitoring the attached and detached ink particles, the parameters taken into account for regulating are the number or surface area of the ink particles measured per unit volume of suspension analyzed (or per unit mass of suspended matter) over all or certain ink-particle size classes.

Advantageously, the monitoring may be based on measurement of the surface areas of ink particles measured in two class sizes, so as to control various ink-removal or ink-detachment steps on the basis of a set of measurements of the various types of ink, according to the regulating possibilities described:

in the filtrates of the separating device; measurement of the fine and coarse detached-ink particles, with a limit between the two size classes preferably lying between 5 and 20 $\mu$m;

in the washed fibers of the separating device; measurement of the fine ink particles attached to the fibers and of the coarse ink particles (black spots in the case of the coarsest ones) which may or may not be bonded to fibers, with a limit between the two size classes preferably lying between 50 and 200 $\mu$m.

The separating device may be used, independently of the ink-monitoring device or otherwise, for regulating bleaching or decoloring operations, on the basis of reflectance measurements on the washed-fiber fraction (measurements of the whiteness and color of the fibers not affected by the color and whiteness of the water and of the fine elements) in the circuits for preparing fresh or recycled pulps or in the circuits of a papermaking machine, including the treatment of broke.

These various examples demonstrate all the advantages of the monitoring device of the invention in regulating a deinking line, especially in terms of effectiveness but also in terms of cost.

We claim:

1. A process for regulating a deinking step in a process line of deinking of recycled paper, said process comprising the steps of:

measuring continuously the quantities of suspended ink particles in two different states, a detached state wherein the ink particles are detached from the fibers within the pulp and an attached state wherein the ink particles are attached to the fibers within the pulp, respectively;

separating the ink particles into divisions of either one of being detached to fibers within the pulp or attached to voluminous fibers within the pulp; and regulating the process line for deinking paper by actuating an operating parameter of at least one of a pulping, hot slushing, washing and flotation step based on the continuous measuring of the ink particles.

2. The process for regulating a deinking step in a process line of deinking of recycled paper according to claim 1, comprising performing the continuous measuring of the attached and detached ink particles at least at either a beginning of the deinking line or after a first deinking step, and during at least either a flotation or a washing, after a second deinking step.

3. The process for regulating a deinking step in a process line of deinking of recycled paper according to claim 1, further comprising refining the regulating by coupling the monitoring of quantities of detached ink particles and attached ink particles with monitoring of the components of the color of the pulp and making adjustments as needed by using a pulp-bleaching step, a pulp-decoloring step or both.

4. A device for continuously measuring a quantity of two different physical states of microscopic particles suspended in a liquid, said device comprising:

a separation assembly having an input portion for receiving liquid from an input pipe, said separation assembly providing means for separating particles according to the size of the particles;

a measurement and process assembly comprising at least two channels or ducts that are connectable to an output portion of said separation assembly, each of said at least two channels or ducts providing passage of a particular size of separated particles toward a measurement zone, and each respective channel comprising a translucent window in the measurement zone;

a measurement and capture unit comprising means for illuminating each translucent window, means for optical recording, and means for digitizing an output of said means for optical recording:

said means for optical recording comprising at least two cameras, each camera being opposite a respective translucent window;

said means for optical recording and said means for illuminating being synchronized so as to capture an image of the translucent window at periodic intervals;

said means for digitizing including means for processing each captured image by a respective camera and digitizing each captured image to determine a size and quantity of particles; and an output unit for receiving data processed by said means for digitizing, said output unit providing data received in at least one of an analog and a digital format so that said output unit is actuable by receipt of the processed data.

5. The device according to claim 4, wherein said separation assembly further includes a means for washing a liquid subjectable to a measuring analysis.

6. A device for continuously measuring a quantity of ink particles in a suspension of paper pulp coming from recycled paper, the ink particles being one of two physical states, detached from fibers within the pulp or attached to fibers within the pulp, said device comprising:

a separation and washing assembly providing means for separating the ink particles into ink-fiber detached stage and ink-fiber attached stage and for washing the ink particles, said separation and washing assembly being continuously fed with paper pulp via an input pipe;

a measurement and process assembly comprising at least two channels or ducts that are connectable to said separation and washing assembly, each one of said at least two channels or ducts providing passage of a particular size of separated particle, and each channel or duct comprising a translucent window in the measurement zone;

a measurement and capture unit comprising means for illuminating each said translucent window, means for optical recording, and means for digitizing an output of said means for optical recording;

said means for optical recording comprising two cameras, each one camera being opposite a respective translucent window;

said means for optical recording and said means for illuminating being synchronized so as to capture an image of said translucent window at periodic intervals;

said means for digitizing including means for processing each captured image by a respective camera and for digitizing each captured image to determine a size and quantity of particles; and an output unit for receiving data processed by said means for digitizing, said output unit providing data received in at least one of an analog and a digital format so that said output device is actuable by receipt of the processed data.

7. The device according to claim 6, wherein said separation and washing assembly further comprises:

a cylindrical microperforated screen located at an input portion of said separation and washing assembly adjacent to the input pipe that continuously conveys the paper pulp to be analyzed;

a declogging and screening rotor having an axis of rotation that is collinear with an axis of the microperforated screen, providing a series of pressure pulses to force the paper pulp onto an internal surface of the screen; and collection and outlet channels, respectively, for a quantity of undiluted detached ink particles, diluted fine elements and washed papermaking fibers having attached ink particles, the washed papermaking fibers being located within an internal volume defined by the screen.

8. The device according to claim 7, wherein said rotor defines a deaeration chamber in a location adjacent to an input portion of said separation and washing assembly wherein the input pipe conveying the paper pulp to be analyzed terminates, and said deaeration chamber communicates with a paper vent for removing a plurality of air bubbles contained in the pulp.

9. The device according to claim 7 further comprising radial disks located on an external peripheral surface of said rotor where a plurality of pipes conveying washing water terminate, said radial disks having openings for controlling a flow of the paper pulp upstream of said screen.

10. The device according to claim 7 further comprising at least one spiraled screw located at a periphery of the rotor in a region located where ducts conveying the washing water terminate.

11. The device according to claim 7 further comprising declogging cylinders located at a periphery of the rotor, said declogging cylinders extending parallel to an axis of rotation of the rotor.

12. The device according to claim 7, wherein said screen further comprises a stationary spiraled channel located downstream of said separation and washing assembly to permit countercurrent washing of the fibers.

13. The device according to claim 6, wherein said separator and washing assembly comprises:

a flat microperforated screen;

a declogging and screening unit providing a series of pressure pulses that force the paper pulp onto the upstream surface of the screen; and collection and outlet channels, respectively, for a quantity of non-diluted detached ink particles, diluted fine elements and washed papermaking fibers having attached ink particles.

14. The device according to claim 13, wherein the declogging and screening unit consists of a rotor having a spiraled channel that rotates and an axis of rotation that is coincident with the center of the screen, so that the rotation of said rotor pumps the paper pulp upstream of the screen and defines a chamber for deaerating said pulp in a central zone.

15. The device according to claim 13, wherein the screen includes a stationary spiraled channel located downstream thereof to permit countercurrent washing of the fibers.

* * * * *